United States Patent
Schumacher et al.

(10) Patent No.: US 6,846,944 B2
(45) Date of Patent: Jan. 25, 2005

(54) PROCESS FOR PREPARING MONOALKYLTIN HALIDES AND DIALKYLTIN HALIDES AND THEIR USE

(75) Inventors: Oliver Schumacher, Werne (DE); Liane Franke, Datteln (DE)

(73) Assignee: Crompton GmbH, Bergkamen (DE)

( * ) Notice: Subject to any disclaimer, the term of this patent is extended or adjusted under 35 U.S.C. 154(b) by 0 days.

(21) Appl. No.: 10/626,819

(22) Filed: Jul. 23, 2003

(65) Prior Publication Data
US 2004/0133022 A1 Jul. 8, 2004

(30) Foreign Application Priority Data
Aug. 8, 2002 (EP) .............................................. 02017845

(51) Int. Cl.$^7$ .................................................. C07F 7/22
(52) U.S. Cl. .......................... 556/104; 556/95; 556/102
(58) Field of Search ........................... 556/95, 102, 104

(56) References Cited

U.S. PATENT DOCUMENTS

| | | | |
|---|---|---|---|
| 3,248,411 A | 4/1966 | Neumann et al. | 260/429.7 |
| 3,894,066 A | 7/1975 | Buschhoff et al. | 260/429.7 |

FOREIGN PATENT DOCUMENTS

| | | |
|---|---|---|
| DE | 1161893 | 1/1964 |
| DE | 2304617 | 8/1974 |
| DE | 2444786 | 4/1976 |
| EP | 1 389 620 A1 * | 2/2004 |
| GB | 1501673 | 2/1978 |
| GB | 2055576 A | 3/1981 |

* cited by examiner

*Primary Examiner*—Porfirio Nazario-Gonzalez
(74) *Attorney, Agent, or Firm*—Michael P. Dilworth

(57) ABSTRACT

The invention relates to a process for the direct preparation of mixtures of monoalkyltin trichlorides $RSnCl_3$ and dialkyltin dichlorides $R_2SnCl_2$ in one reaction step by partial alkylation of tin tetrachloride using alkylaluminum compounds in the form of their ether donor complexes, wherein an amount of ether greater than that required for stoichiometric formation of the donor complex is used in the reaction.

7 Claims, No Drawings

PROCESS FOR PREPARING MONOALKYLTIN HALIDES AND DIALKYLTIN HALIDES AND THEIR USE

Mixtures of monoalkyltin trichlorides $RSnCl_3$ and dialkyltin dichlorides $R_2SnCl_2$ are of great industrial importance as raw materials for the production of catalysts and as heat stabilizers for polymers based on organotin mercaptides, organotin carboxylates and organotin oxides.

Methyltin compounds, butyltin compounds and octyltin compounds are of particular industrial importance. In addition, numerous countries permit the use of dodecyltin compounds as heat stabilizers for PVC in indirect contact with food. The pure monoalkyltin or dialkyltin compounds are used only rarely as heat stabilizers for PVC, but instead use is usually advantageously made of mixtures of monoalkyltin and dialkyltin compounds which synergistically supplement and aid one another's action. The optimum ratio of monoalkyltin to dialkyltin compound in this case depends on the respective PVC type and formulation, the method of processing and the requirement profile, and also on the formulation of the PVC stabilizer.

Mixtures of monoalkyltin oxides and dialkyltin oxides, for example, are employed as catalysts in the preparation of polyesters.

Only in the case of the methyltin compounds are mixtures of monoalkyltin trichlorides and dialkyltin dichlorides obtainable in one step by a direct route.

In the case of higher alkyltin compounds (with alkyl groups $C_nH_{2n+1}$ where n=4 or longer), the preparation of the mixtures of monoalkyltin trichlorides and dialkyltin dichlorides is carried out in multistage processes.

According to the prior art, tetraalkyltin compounds $R_4Sn$ and/or trialkyltin chlorides $R_3SnCl$ are prepared in a first step by alkylation of tin tetrachloride. Alkylating agents used are either organomagnesium compounds, RMgCl, or particularly economically organoaluminum compounds, $AlR_3$.

In a second step, the mixtures of monoalkyltin trichlorides and dialkyltin dichlorides are then prepared by a comproportionation reaction of the tetraalkyltin compounds $R_4Sn$ and/or the trialkyltin chlorides $R_3SnCl$ with further tin tetrachloride (cf. DE 1 161 893).

In the case of relatively long-chain alkyltin compounds (with alkyl groups $C_nH_{2n+1}$ where n=4 or longer), mixtures having various ratios of monoalkyltin trichlorides and dialkyltin dichlorides can be prepared by means of this comproportionation reaction. When trialkyltin chlorides are used, the maximum monoalkyltin trichloride content which can be achieved in this way is 50 mol %, and when tetraalkyltin compounds are used, the maximum monoalkyltin trichloride content which can be achieved is 67 mol %.

Mixtures of monoalkyltin trichlorides and dialkyltin dichlorides having monoalkyltin trichloride contents of more than 67 mol % cannot be obtained in this way.

In principle, it is possible to prepare such mixtures by fractionating mixtures having lower monoalkyltin trichloride contents, for example by distillation. This procedure is subject to limits because the boiling points of the alkyltin chlorides increase greatly with increasing chain length and number of alkyl groups and the thermal decomposition of the alkyltin chlorides becomes significant as a secondary reaction at above about 200° C.

In the case of still longer-chain alkyltin compounds (with alkyl groups $C_nH_{2n+1}$ where n=8 or longer), such distillations can no longer be carried out economically.

A particularly important factor for the usability of the mixtures of monoalkyltin trichlorides and dialkyltin dichlorides for preparing heat stabilizers for PVC is a very low content of tin tetrachloride, trialkyltin compounds and tetraalkyltin compounds.

Trialkyltin compounds have the disadvantage of generally being significantly more toxic than monoalkyltin and dialkyltin compounds and are therefore undesirable. Trialkyltin and tetraalkyltin compounds display no effect in the heat stabilization of PVC. In the preparation of heat stabilizers for PVC, tin tetrachloride forms inorganic tin compounds which have no effect in the heat stabilization of PVC and in addition can even impair the effectiveness of the stabilizers.

GB 1501673 (=DE 2 444 786) teaches that monoalkyltin trichlorides $RSnCl_3$ can also be prepared directly by monoalkylation of tin tetrachloride using stoichiometric amounts of alkylaluminum compounds in the form of their donor complexes with ethers or tertiary amines at mild temperatures.

GB 1501673 (comparison example 3) also teaches that the preparation of dialkyltin compounds by an analogous route is not successful. When an attempt is made to force the formation of pure dialkyltin compounds by doubling the amount of the alkylaluminum-donor complex, the result is instead a product mixture of monoalkyltin trichloride $RSnCl_3$, dialkyltin dichloride $R_2SnCl_2$, trialkyltin chloride $R_3SnCl$ and tetraalkyltin $R_4Sn$.

Furthermore, GB 1501673 teaches that when ethers are used as complexing agents, it is necessary to use only the stoichiometric amount of ether required for the formation of the alkylaluminum-donor complex, and that increasing the amount of ether above this has no effects on the composition of the product mixture but merely makes the work-up of the reaction mixture (phase separation, extraction) easier.

In addition, GB 1501673 maintains that mixtures of monoalkyltin trichlorides and dialkyltin dichlorides can be prepared directly by alkylation of tin tetrachloride using stoichiometric amounts of alkyl-aluminum compounds in the form of their donor complexes with ethers at elevated temperature. However, examination of the starting material stoichiometry and the product composition in example 19 shows that only part of the reactants used can have reacted. The exclusively gas-chromatographic analysis of the product did not in this case take account of losses of the $SnCl_4$ used; the yield based on the tin used must therefore have been significantly lower than that reported.

It is an object of the present invention to find a process for preparing mixtures of monoalkyltin trichlorides and dialkyltin dichlorides having high monoalkyltin trichloride contents, particularly for long-chain alkyltin compounds (with alkyl groups $C_nH_{2n+1}$ where n=8 or longer).

A further object is to find a single-stage process which does not suffer from the economic disadvantages of the multistage procedure of the prior art.

Furthermore, it is an object of the invention to find a process which, in particular, makes it possible to prepare mixtures of monoalkyltin trichlorides and dialkyltin dichlorides having low contents of trialkyltin chlorides and tin tetrachloride.

It has surprisingly been found that mixtures of monoalkyltin trichlorides $RSnCl_3$ and dialkyltin dichlorides $R_2SnCl_2$ can be prepared directly in one reaction step by partial alkylation of tin tetrachloride using alkyl-aluminum compounds in the form of their ether donor complexes when a larger amount of ether than that required for the stoichiometric formation of the donor complex is used in the reaction.

Appropriate choices of the ratios of reactants and the reaction conditions make it possible to prepare mixtures according to the invention having monoalkyltin trichloride contents of from 45 mol % to above 99 mol % in one step in a direct process.

In a preferred embodiment of the process of the invention, the molar excess of ether is chosen so that the excess is at least 10 mol % of the stoichiometric ratio of trialkylaluminum compound and the donor ether.

Furthermore, the process is preferably carried out in the temperature range from 40 to 70° C.

In addition, the donor or complexing agent used is preferably di-n-butyl ether.

The present invention further provides mixtures of monoalkyltin trichlorides $RSnCl_3$ and dialkyltin dichlorides $R_2SnCl_2$ obtainable by a process as described above in which the process yield is at least 90 mol %, in particular at least 95 mol %, based on the amount of tin tetrachloride used.

Preference is given to mixtures of monoalkyltin trichlorides $RSnCl_3$ and dialkyltin dichlorides $R_2SnCl_2$ having monoalkyltin trichloride contents of at least 50 mol %, in particular at least 65 mol %.

Furthermore, the alkyltin chlorides in the mixtures bear alkyl groups $C_nH_{2n+1}$ where n=8 to 18, in particular n=10 to 18.

The mixtures of monoalkyltin trichlorides $RSnCl_3$ and dialkyltin dichlorides $R_2SnCl_2$ also have a trialkyltin chloride content of up to 5 mol % and a tin tetrachloride content of less than 5 mol %.

The invention further provides mixtures of monoalkyltin trichlorides $RSnCl_3$ and dialkyltin dichlorides $R_2SnCl_2$ having a monoalkyltin trichloride content of at least 50 mol %, a dialkyltin dichloride content of at least 20 mol % and a trialkyltin chloride content of up to 5 mol %.

Particular preference is given to using the mixtures of monoalkyltin trichlorides and dialkyltin dichlorides prepared according to the invention for the preparation of mixtures of monoalkyltin tris(mercaptides) and dialkyltin bis(mercaptides):

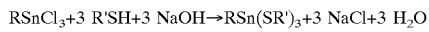

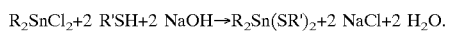

These monoalkyltin tris(mercaptides) and dialkyltin bis(mercaptides) are used as heat stabilizers for PVC and also as polyurethane catalysts.

EXAMPLES

The following examples illustrate the invention without restricting it. Parts and percentages are by weight unless indicated otherwise.

Example 1 (According to the Invention)

A mixture is firstly prepared from 65.1 g of di-n-butyl ether (0.5 mol) and 270.7 g of tridodecylaluminum (technical grade having a $(C_{12}H_{25})_3Al$ content of 89%, corresponding to 0.447 mol, contamination mainly due to hydrocarbons).

260.5 g (1 mol) of $SnCl_4$ are placed in a 1 l three-neck flask provided with stirrer, Claisen attachment, thermometer, reflux condenser and dropping funnel, and the above mixture is added at 50° C. while stirring and cooling. After the addition is complete, the mixture is stirred at 50° C. for a further 30 minutes. After cooling to room temperature, the reaction mixture is added to a mixture of 117 g of di-n-butyl ether (0.9 mol) and 180 g of water while cooling.

The phases are separated and the aqueous phase is discarded. The di-n-butyl ether is distilled off from the organic phase at 20 mbar and a maximum of 120° C. to give a mixture consisting predominantly of monododecyltin trichloride and didodecyltin dichloride.

Gas-chromatographic analysis of a sample which had been converted into the ethyl derivative by means of ethylmagnesium chloride indicated the following product composition:

| | |
|---|---|
| $(C_{12}H_{25})SnCl_3$ | 63.3 mol %, |
| $(C_{12}H_{25})_2SnCl_2$ | 21.8 mol %, |
| $(C_{12}H_{25})_3SnCl$ | 3.3 mol %, |
| Hydrocarbons | 11.6 mol %. |

Elemental analysis indicated a content of 24.5% of Sn and 19.7% of Cl.

The yield is 459 g (95.3% based on the amount of tin tetrachloride used).

Example 2 (According to the Invention)

A mixture is firstly prepared from 64.3 g of di-n-butyl ether (0.5 mol) and 272.5 g of tridodecylaluminum (technical grade having a $(C_{12}H_{25})_3Al$ content of 89%, corresponding to 0.45 mol, contamination mainly due to hydrocarbons).

260.5 g (1 mol) of $SnCl_4$ are placed in a 1 l three-neck flask provided with stirrer, Claisen attachment, thermometer, reflux condenser and dropping funnel, and the above mixture is added at 50° C. while stirring and cooling. After the addition is complete, the mixture is stirred at 50° C. for a further about 30 minutes, and 117 g of di-n-butyl ether (0.9 mol) are then likewise added dropwise while stirring. After this addition is complete, the mixture is then stirred without heating for a further 15 minutes. The reaction mixture is subsequently poured into 180 ml of ice water while cooling. During this procedure, the temperature is maintained at not more than 50–70° C.

The phases are separated and the aqueous phase is discarded. The di-n-butyl ether is distilled off from the organic phase at 20 mbar and a maximum of 120° C. to give a mixture consisting predominantly of monododecyltin trichloride and didodecyltin dichloride.

Gas-chromatographic analysis of a sample which had been converted into the ethyl derivative by means of ethylmagnesium chloride indicated the following product composition:

| | |
|---|---|
| $(C_{12}H_{25})SnCl_3$ | 62.1 mol %, |
| $(C_{12}H_{25})_2SnCl_2$ | 23.3 mol %, |
| $(C_{12}H_{25})_3SnCl$ | 2.9 mol %, |
| Hydrocarbons | 11.7 mol %. |

Elemental analysis indicated a content of 24.6% of Sn and 19.6% of Cl.

The yield is 463 g (95.8% based on the amount of tin tetrachloride used).

Example 3 (According to the Invention)

A mixture is firstly prepared from 174 g of di-n-butyl ether (1.34 mol) and 272.5 g of tridodecylaluminum (technical grade having a $(C_{12}H_{25})_3Al$ content of 89%, corresponding to 0.45 mol, contamination mainly due to hydrocarbons).

260.5 g (1 mol) of $SnCl_4$ are placed in a 1 l three-neck flask provided with stirrer, Claisen attachment, thermometer, reflux condenser and dropping funnel, and the above mixture is added at 50° C. while stirring and cooling. After the addition is complete, the mixture is stirred at 50° C. for a further 45 minutes. After cooling to room temperature, the reaction mixture is added to 140 g of water while cooling.

The phases are separated and the aqueous phase is discarded. The di-n-butyl ether is distilled off from the organic phase at 20 mbar and a maximum of 120° C. to give a mixture consisting predominantly of monododecyltin trichloride and didodecyltin dichloride.

Gas-chromatographic analysis of a sample which had been converted into the ethyl derivative by means of ethylmagnesium chloride indicated the following product composition:

| | |
|---|---|
| $(C_{12}H_{25})SnCl_3$ | 63.7 mol %, |
| $(C_{12}H_{25})_2SnCl_2$ | 25.7 mol %, |
| $(C_{12}H_{25})_3SnCl$ | 0.6 mol %, |
| Hydrocarbons | 10.0 mol %. |

Elemental analysis indicated a content of 25.15% of Sn and 20.3% of Cl.

The yield is 456.4 g (96.7% based on the amount of tin tetrachloride used).

Example 4 (According to the Invention)

A mixture is firstly prepared from 174 g of di-n-butyl ether (1.34 mol) and 165 g of trioctylaluminum (corresponding to 0.45 mol).

260.5 g (1 mol) of $SnCl_4$ are placed in a 1 l three-neck flask provided with stirrer, Claisen attachment, thermometer, reflux condenser and dropping funnel, and the above mixture is added at 50° C. while stirring and cooling. After the addition is complete, the mixture is stirred at 50° C. for a further 45 minutes. After cooling to room temperature, the reaction mixture is added to 140 g of water while cooling.

The phases are separated and the aqueous phase is discarded. The di-n-butyl ether is distilled off from the organic phase at 20 mbar and a maximum of 120° C. to give a mixture consisting predominantly of monooctyltin trichloride and dioctyltin dichloride.

Gas-chromatographic analysis of a sample which had been converted into the ethyl derivative by means of ethylmagnesium chloride indicated the following product composition:

| | |
|---|---|
| $(C_8H_{17})SnCl_3$ | 66.3 mol %, |
| $(C_8H_{17})_2SnCl_2$ | 32.0 mol %, |
| $(C_8H_{17})_3SnCl$ | 0.4 mol %, |
| Hydrocarbons | 1.3 mol %. |

Elemental analysis indicated a content of 32.3% of Sn and 25.8% of Cl.

The yield is 360.2 g (98.1% based on the amount of tin tetrachloride used).

The aqueous phase was analyzed by AAS (atomic absorption spectrometry). It contained 0.13 g of tin, corresponding to 0.29 g of $SnCl_4$ or about 0.11% of the amount of tin used.

Example 5 (According to the Invention)

A mixture is firstly prepared from 174 g of di-n-butyl ether (1.34 mol) and 354.4 g of trioctadecylaluminum (corresponding to 0.45 mol).

260.5 g (1 mol) of $SnCl_4$ are placed in a 1 l three-neck flask provided with stirrer, Claisen attachment, thermometer, reflux condenser and dropping funnel, and the above mixture is added at 50° C. while stirring and cooling. After the addition is complete, the mixture is stirred at 50° C. for a further 45 minutes. After cooling to room temperature, the reaction mixture is added to 140 g of water while cooling.

The phases are separated and the aqueous phase is discarded. The di-n-butyl ether is distilled off from the organic phase at 20 mbar and a maximum of 120° C. to give a mixture consisting predominantly of monooctadecyltin trichloride and dioctadecyltin dichloride.

Gas-chromatographic analysis of a sample which had been converted into the ethyl derivative by means of ethylmagnesium chloride indicated the following product composition:

| | |
|---|---|
| $(C_{18}H_{37})SnCl_3$ | 67.7 mol %, |
| $(C_{18}H_{37})_2SnCl_2$ | 30.5 mol %, |
| $(C_{18}H_{37})_3SnCl$ | 0.5 mol %, |
| Hydrocarbons | 1.3 mol %. |

Elemental analysis indicated a content of 21.4% of Sn and 17.1% of Cl.

The yield is 528.6 g (95.3% based on the amount of tin tetrachloride used).

Example 6 (According to the Invention)

Example 4 according to the invention was repeated using other ethers in place of di-n-butyl ether.

Experimental conditions, yields and product compositions are summarized in Table 1.

Example 7 (According to the Invention)

Example 4 according to the invention was repeated at higher temperatures.

Experimental conditions, yields and product compositions are summarized in Table 2.

Example 8 (According to the Invention)

Example 4 according to the invention was repeated with the reactant ratios $SnCl_4$/tri-n-octylaluminum/di-n-butyl ether being varied.

Experimental conditions, yields and product compositions are summarized in Table 3.

TABLE 1

| Example | Ether | Product Maximum temperature [° C.] | Product yield [g]/ (% of theory) | Sn [% by mass] | Cl [% by mass] | $(C_8H_{17})SnCl_3$ [mol %] | $(C_8H_{17})_2SnCl_2$ [mol %] | $(C_8H_{17})_3SnCl$ [mol %] | Hydrocarbons [mol %] |
|---|---|---|---|---|---|---|---|---|---|
| 6 a | Diethyl ether | 35 | 348.6/(93.7) | 31.9 | 24.7 | 63.1 | 31.7 | 4.6 | 0.7 |
| 6 b | Methyl tert-butyl ether | 60 | 361.3/(98.0) | 32.2 | 25.5 | 65.0 | 32.8 | 0.6 | 1.6 |
| 6 c | Tetrahydrofuran | 60 | 353.8/(95.6) | 32.1 | 25.3 | 64.0 | 33.3 | 0.9 | 1.8 |
| 6 d | Dioxane | 60 | 357.6/(97.3) | 32.3 | 25.7 | 65.8 | 32.4 | 0.7 | 1.1 |

TABLE 2

| Example | Product Maximum temperature [° C.] | Product yield [g]/ (% of theory) | Sn [% by mass] | Cl [% by mass] | $(C_8H_{17})SnCl_3$ [mol %] | $(C_8H_{17})_2SnCl_2$ [mol %] | $(C_8H_{17})_3SnCl$ [mol %] | Hydrocarbons [mol %] |
|---|---|---|---|---|---|---|---|---|
| 7 a | 70 | 358.1/(96.8) | 32.1 | 25.3 | 64.3 | 32.7 | 1.4 | 1.6 |
| 7 b | 100 | 351.1/(94.4) | 31.9 | 24.9 | 66.0 | 25.3 | 8.4 | 0.3 |

TABLE 3

| Example | Tri-n-octyl-aluminum used [g]/([mol]) | Di-n-butyl ether used [g]/([mol]) | Product yield [g]/ ([% of theory]) | Sn [% by mass] | Cl [% by mass] | $(C_8H_{17})SnCl_3$ [mol %] | $(C_8H_{17})_2SnCl_2$ [mol %] | $(C_8H_{17})_3SnCl$ [mol %] | Hydrocarbons [mol %] |
|---|---|---|---|---|---|---|---|---|---|
| 8 a | 191.0/(0.521) | 201.5/(1.55) | 374.7/(89.0) | 28.2 | 20.5 | 38.0 | 46.5 | 0.8 | 14.7 |
| 8 b | 172.2/(0.470) | 181.7/(1.40) | 365.6/(93.2) | 30.3 | 23.4 | 54.3 | 36.2 | 0.6 | 8.9 |
| 8 c | 153.7/(0.419) | 162.1/(1.24) | 356.6/(95.7) | 31.8 | 26.1 | 70.2 | 23.4 | 0.4 | 6.0 |
| 8 d | 134.7/(0.367) | 142.1/(1.09) | 341.0/(98.0) | 34.1 | 29.5 | 89.2 | 9.9 | 0.1 | 0.8 |

Comparative Example 1

A mixture is firstly prepared from 58.2 g of di-n-butyl ether (0.45 mol) and 270.7 g of tridodecylaluminum (technical grade having a $(C_{12}H_{25})_3Al$ content of 89%, corresponding to 0.447 mol, contamination due to hydrocarbons).

260.5 g (1 mol) of $SnCl_4$ are placed in a 1 l three-neck flask provided with stirrer, Claisen attachment, thermometer, reflux condenser and dropping funnel, and the above mixture is added at 50° C. while stirring and cooling. After the addition is complete, the mixture is stirred at 50° C. for a further 30 minutes. After cooling to room temperature, the reaction mixture is added to a mixture of 117 g of di-n-butyl ether (0.9 mol) and 180 g of water while cooling.

The phases are separated and the aqueous phase is discarded. The di-n-butyl ether is distilled off from the organic phase at 20 mbar and a maximum of 120° C. to give a mixture consisting predominantly of monododecyltin trichloride and didodecyltin dichloride.

Gas-chromatographic analysis of a sample which had been converted into the ethyl derivative by means of ethylmagnesium chloride indicated the following product composition:

| | |
|---|---|
| $(C_{12}H_{25})SnCl_3$ | 69.3 mol %, |
| $(C_{12}H_{25})_2SnCl_2$ | 18.5 mol %, |
| $(C_{12}H_{25})_3SnCl$ | 6.3 mol %, |
| Hydrocarbons | 5.9 mol %. |

Elemental analysis indicated a content of 25.8% of Sn and 20.6% of Cl.

The yield is 427 g (92.9% based on the amount of tin tetrachloride used).

Thus, if only a virtually equimolar amount of ether is used, products having disadvantageously high trialkyltin contents are obtained. In addition, the yield drops in comparison with the examples according to the invention.

What is claimed is:

1. A process for the direct preparation of mixtures of monoalkyltin trichlorides $RSnCl_3$ and dialkyltin dichlorides $R_2SnCl_2$ in one reaction step by partial alkylation of tin tetrachloride using alkylaluminum compounds in the form of their ether donor complexes, wherein an amount of ether greater than that required for stoichiometric formation of the donor complex is used in the reaction.

2. The process as claimed in claim 1, wherein mixtures having monoalkyltin trichloride contents of from 45 mol % to above 99 mol % are prepared in one step in a direct process.

3. The process as claimed in claim 1, wherein the molar excess of ether is at least 10 mol % over the stoichiometric ratio of trialkylaluminum compound and donor ether.

4. The process as claimed in claim 1, wherein the reaction is carried out in a temperature range from 40° C. to 70° C.

5. The process as claimed in claim 1, wherein the donor complexing agent used is di-n-butyl ether.

6. A mixture of monoalkyltin trichlorides $RSnCl_3$ and dialkyltin dichlorides $R_2SnCl_2$ having a trialkyltin chloride content of up to 5 mol %.

7. A mixture of monoalkyltin trichlorides $RSnCl_3$ and dialkyltin dichlorides $R_2SnCl_2$ having a monoalkyltin trichloride content of at least 50 mol %, a dialkyltin dichloride content of at least 20 mol % and a trialkyltin chloride content of up to 5 mol %.

* * * * *